United States Patent [19]
Leis

[11] Patent Number: 5,923,417
[45] Date of Patent: *Jul. 13, 1999

[54] SYSTEM FOR DETERMINING THE SPATIAL POSITION OF A TARGET

[75] Inventor: Stephen Eldon Leis, Waterloo, Canada

[73] Assignee: Northern Digital Incorporated, Ontario, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/938,098

[22] Filed: Sep. 26, 1997

[51] Int. Cl.⁶ .............................. G01B 11/26; G01C 1/00
[52] U.S. Cl. .................................... 356/141.1; 356/141.2; 356/141.5
[58] Field of Search ............................. 356/141.1, 141.2, 356/139.03, 141.5

[56] References Cited

U.S. PATENT DOCUMENTS

| | | |
|---|---|---|
| 3,799,676 | 3/1974 | Chatterton . |
| 3,876,308 | 4/1975 | Alpers . |
| 4,396,945 | 8/1983 | DiMatteo et al. ........................ 358/107 |
| 5,557,347 | 9/1996 | Johnson . |
| 5,614,912 | 3/1997 | Mitchell ................................... 342/146 |
| 5,675,112 | 10/1997 | Giry et al. ............................... 89/41.06 |
| 5,685,504 | 11/1997 | Schneider et al. . |

FOREIGN PATENT DOCUMENTS

2718519-A1  4/1994  France ............................... F41G 3/02

OTHER PUBLICATIONS

Original Instruments Product Literature; "The Dynasight Sensor"; Grand Praire, Texas; Feb. 7, 1999.

PCT Search Report for Related PCT Application PCT/CA 98/00911.

*Primary Examiner*—Stephen C. Buczinski
*Attorney, Agent, or Firm*—Fish & Richardson P.C.

[57] ABSTRACT

A system for determining the spatial position of a target having an active target adapted to emit energy in response to an active signal and a passive target adapted to reflect energy impinging upon such passive target from an active energy source. A common energy detector is provided for detecting both the energy emitted by the active target and the energy reflected by the passive target. A common processor is provided for determining the spatial positions of both the passive and active targets in response to the energy detected by the common detector. During a sensor cycle the spatial position of the active target is determined and during a sensor cycle the position of the passive target is determined. The sensor cycles may be interspersed or may be the same cycle to enable simultaneous determination of both the active target and the passive target during a single sensor cycle. The system also enables the determination of the spatial position and angular orientation of both a rigid object having affixed thereto active targets and/or another rigid object having affixed thereto passive targets and/or an object having affixed thereto both an active and passive targets.

10 Claims, 6 Drawing Sheets

SYSTEM FOR DETERMINING THE SPATIAL POSITION OF A TARGET

BACKGROUND OF THE INVENTION

This invention relates generally to systems for determining the spatial position of a target and more particularly to systems of such type which are adapted to determine the spatial position of both active and passive targets. Still more particularly, the invention relates to systems adapted to determine the spatial positions and angular orientations of one object having active targets mounted thereto and another object having passive targets mounted thereto.

As is known in the art, systems are available for determining the spatial position and angular orientation of an object. One such system includes passive retro-reflectors as point markers, or targets, affixed to the object and a second system includes active radiating emitters as the affixed point markers, or targets. Both techniques operate by projecting the image of a high contrasting target onto spaced sensors and using mathematical processing to determine the three dimensional coordinates of each one of the point targets. These three dimensional coordinates (i.e., 3D) are then used as discrete points, or may be considered as a set if their geometric arrangement is known, resulting in the determination of the position and angular orientation of the object (i.e., six degrees of freedom: x, y and z positions and pitch, yaw and roll angular orientations) in space relative to a three dimensional coordinate system centered at a preselected point in space, typically at a point fixed relative to the sensors.

Both active and passive targets operate by projecting the image of a high contrasting target onto spaced sensors and use mathematical processing to determine the spatial position of each one of the targets relative to a three dimensional coordinate system the origin of which is at a pre-selected point in space, typically at a point fixed relative to the sensors. The spatial positions of the targets can be used in many applications. For example, several discrete targets can be affixed to points of interest on a human subject. The human subject can then conduct a series of motions while the system determines spatial position data for each of the various targets affixed to the human subject. The data can be graphically displayed and/or collected and stored for use in a multitude of applications. One of the uses for the data is to provide information to medical professionals conducting medical assessments or diagnosis of the subject's movements. Another use for the data collected is to transfer it to a computer animation software package to create movements in an animated character which are comparable to those made by the human subject. In another example, two or more of the targets may be rigidly affixed to an object in a known geometric arrangement. The system then considers the rigidly affixed targets as a set resulting in the determination of the spatial position of the object and, in the case where two targets are used, the vector angle of the object or, in the case where three or more targets are used, the angular orientation of the object. Determining the spatial position and either the vector angle or angular orientation of an object has several uses. For example, a pointing device can be made out of the object whereby the end tip of the pointing device is in a known position relative to the targets. Such a pointing device can be used as a digitizing pointer held by hand as in reverse engineering applications. An operator moves this pointing object to various known places on a manufactured component and the accuracy of the manufacturing processes is determined from analysis of the determined end tip position of the pointing device.

In one emitting target (i.e., active target) system, multiple charge couple device (CCD) sensors are used to detect the energy emitted by the target. A single point target is energized per sensor cycle to emit infrared energy. During each sensor cycle, the emitted energy focused onto the sensor is collected (i.e. integrated) and shifted to the sensor processing circuitry. In order to determine the 3D position of the target, the target must be detected on at least three sensor axes (i.e. to cover a minimum of 3 orthogonal planes). There are many advantages to a system which uses emitting targets including high contrast images being produced on the sensors, control over activation of each of the targets affording positive and automatic target discrimination, and the ability to use high speed linear sensors. These systems, however, are designed to work with only active point targets.

In one retro-reflective target (i.e., passive target) system, an energy source is energized to emit infrared energy in the general direction of the retro-reflective target. Multiple CCD sensors are then used to detect the energy reflected by the target. During each sensor cycle, the reflected energy focused onto the sensor is collected (i.e., integrated) and shifted to the sensor processing circuitry. In order to determine the 3D position of the target, the target must be detected on at least three sensor axes (i.e. to cover a minimum of 3 orthogonal planes). There are many advantages to a retro-reflective target system including the use of wireless targets and the ability to use inexpensive low speed area array sensors. These systems, however, are designed to work with only passive point targets.

In some applications, such as in an image guided surgical procedure where instrument pose is being tracked with respect to the patient, certain surgical instruments have affixed to them active targets and other surgical instruments have affixed to them passive targets. Thus, when the surgeon is performing a procedure during an operation which requires an instrument having passive targets, such instrument, along with its sensors, processor and display are used by the surgeon. Once that procedure is performed and the surgeon requires an instrument having passive targets, such instrument along with its sensors, processors and display are used by the surgeon.

SUMMARY OF THE INVENTION

In accordance with the present invention, a system for determining the spatial position of a target is provided having an active target adapted to emit energy in response to an activation signal and a passive target adapted to reflect energy impinging upon such passive target from an activatable energy source. A common energy detector is provided for detecting both the energy emitted by the active target and the energy reflected by the passive target. A common processor is provided for determining the spatial positions of both the passive and active targets in response to the energy detected by the common detector. During a sensor cycle the spatial position of the active target is determined and during a sensor cycle the position of the passive target is determined. The sensor cycles may be interspersed, or the sensor cycle may be the same to enable simultaneous detection of both the active target and the passive target during a single sensor cycle.

In accordance with another feature of the invention, a system is provided for determining the spatial position and angular orientation of a rigid object having affixed thereto active targets and/or a rigid object having affixed thereto passive targets and/or a rigid body having affixed thereto both a passive target and an active target. The active and passive targets are affixed to their respective rigid objects in known, fixed relationship to each other and to the geometry of the object. A common energy detector is provided for detecting the energy emitted by the active targets affixed to one object, the energy reflected by the passive target affixed to the other object or both the energy emitted from the active target and the energy reflected by the passive target which are affixed to the same rigid body. A common processor is provided for determining the spatial position of the object in response to the energy detected by the common detector. During a sensor cycle the spatial position of the active target is determined and during a sensor cycle the position of the passive target is determined. The sensor cycles may be interspersed, or the sensor cycles may be the same to enable simultaneous detection of both the active target and the passive target during a single sensor cycle.

In accordance with another feature of the invention, a display is provided for depicting the determined spatial orientation and position of the objects having active and passive targets.

With such arrangement, the use of a common detector for both the active and passive targets enables the common processor to use the same processing steps in determining the spatial orientation of both the active and passive target affixed objects. Further, in a surgical environment, the surgeon has a system adapted to operate with both active and passive targets and is thereby able to view on a common display one instrument having active targets affixed to it, and/or another instrument having passive targets affixed to it and/or another object having both active and passive targets affixed to it.

BRIEF DESCRIPTION OF THE DRAWINGS

Other features of the invention will become more readily apparent with reference to the following description taken together with the following drawings, in which:

FIG. 5C showing an interspersed active-passive mode and FIG. 5D showing a simultaneous active-passive mode;

DESCRIPTION OF THE PREFERRED EMBODIMENTS

Figure 1:
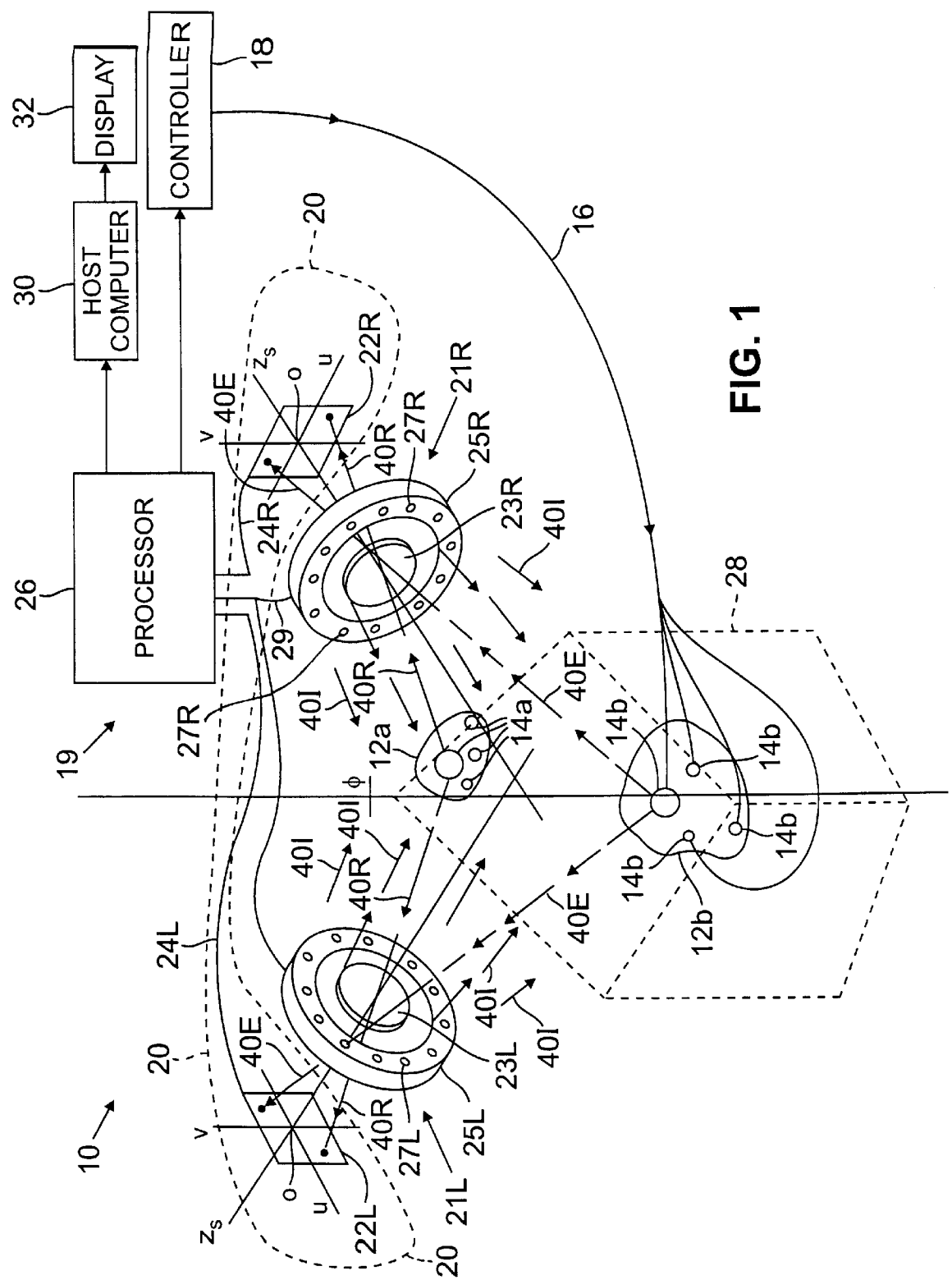
FIG. 1 is a block diagram of a system for determining the spatial position and orientation of a pair of rigid objects according to the invention.

Referring now to FIG. 1, a system 10 for determining the spatial position and orientation of either or both of a pair of rigid object 12a, 12b is provided. Here, the rigid objects 12a, 12b are different surgical instruments. Here, rigid body 12a has a plurality of, here four, passive, retro-reflecting point targets 14a affixed thereto. Here, each of the energy retro-reflecting targets 14a includes a sphere, affixable to object 12a, covered with a retro-reflective material as is generally available and well known in the art. As is also known in the art, other types of energy retro-reflecting targets are available such as flat disks affixable to the object 12a, covered with a retro-reflective material as is generally available. The targets 14a are affixed to object 12a in a known, fixed relationship to each other and to the geometry of the object 12a.

Here, rigid body 12b has a plurality of active point targets 14b affixed thereto. The targets 14b are affixed to object 12b in a known, fixed relationship to each other and to the geometry of the object 12b. The active targets 14b are fed via a cable 16 to a controller 18, as shown. Here, the energy emitting targets 14b include an infrared energy emitting diode which, upon being energized with electrical energy fed thereto by controller 18 via cable 16, emits infrared light energy. Such infrared energy emitting diodes are generally available and well known in the art.

Figure 2:
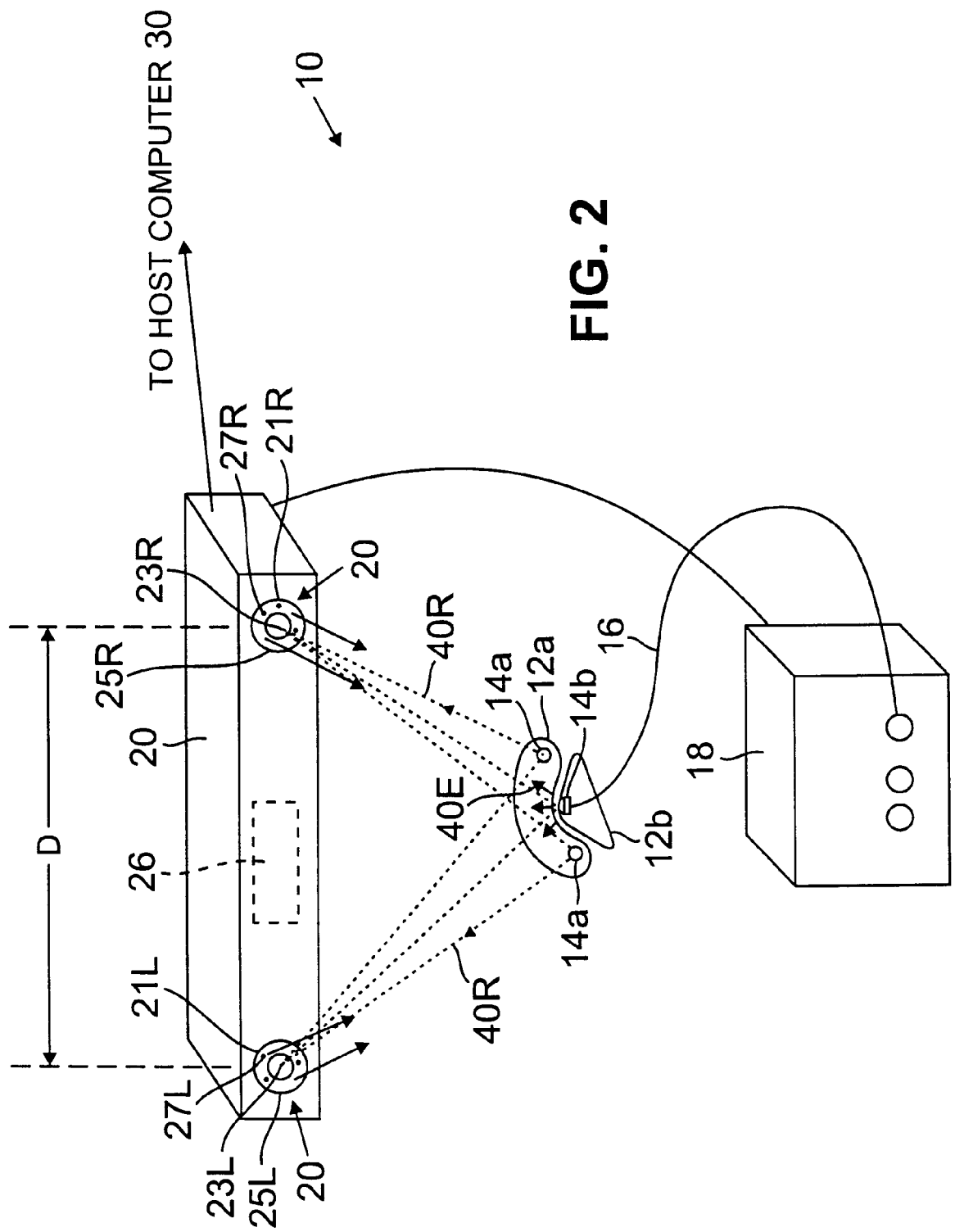
FIGS. 2 and 3 are diagrammatic sketches of the system of FIG. 1.
Figure 3:
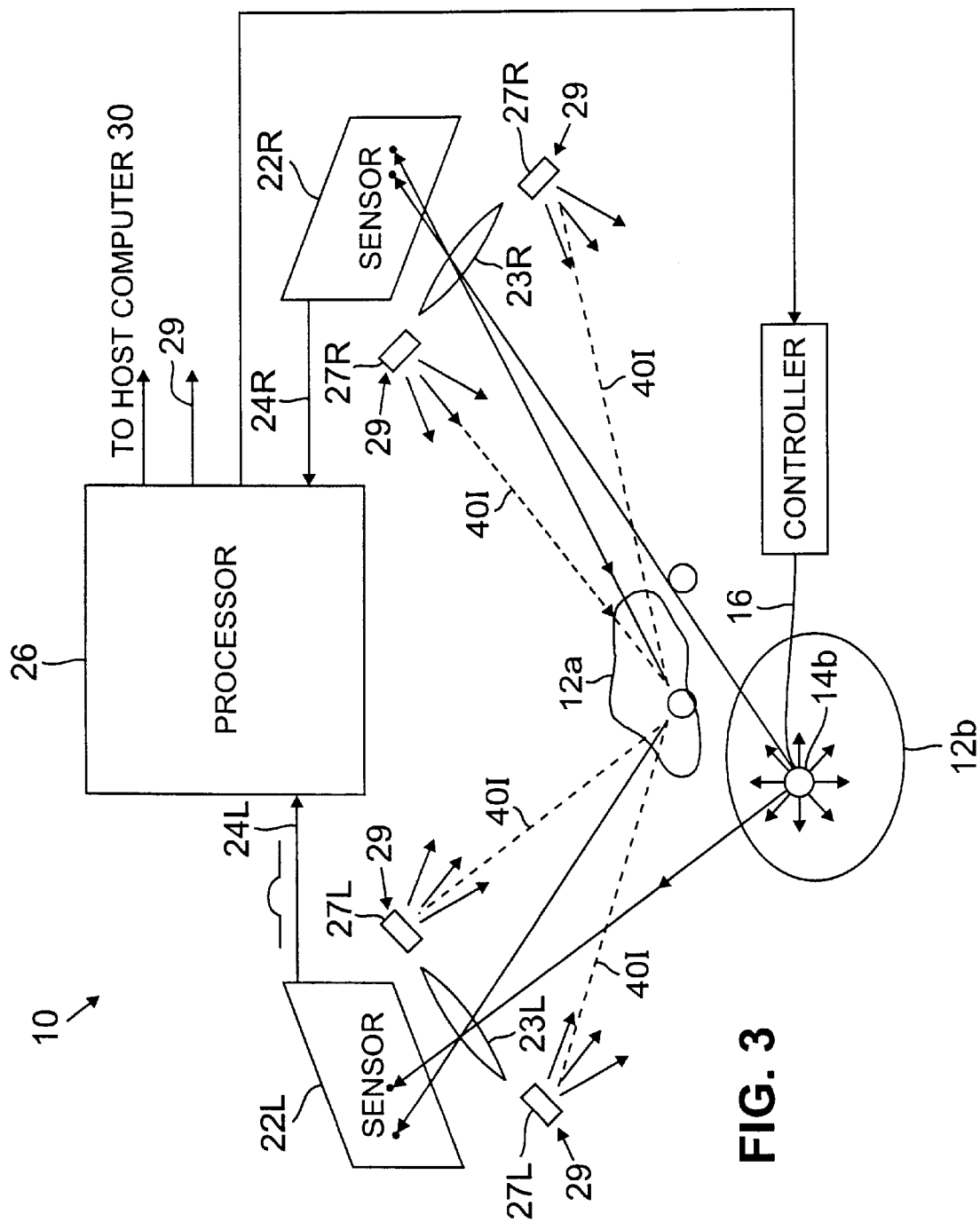

Referring also to FIG. 2, a common energy detection system 20 is provided for detecting both the energy emitted by the active targets 14b affixed to object 12b and the energy reflected by the passive targets 14a affixed to the other object 12a. The common detector system 20 includes a pair of spaced sensor assemblies 21L and 21R. Each one of the sensor assemblies 21L, 21R includes: a, here two two-dimensional, charge couple device (CCD) sensor 22L, 22R (FIGS. 1 and 3), respectively; an annular mounting ring 25L, 25R, respectively; a focusing lens 23L, 23R mounted centrally within the annular mounting ring 25L, 25R, respectively, as shown; and, a plurality of light emitting diodes 27L, 27R mounted to a respective one of the annular mounting rings 25L, 25R, as shown.

Figure 4:
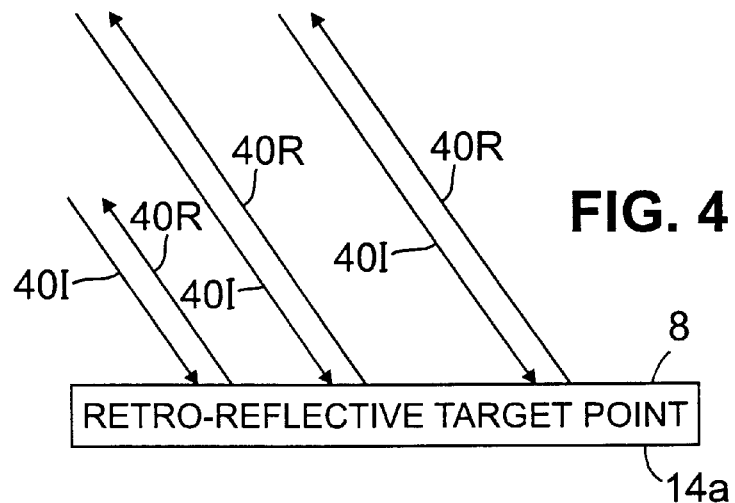
FIG. 4 is a diagram useful in understanding the retro-reflective characteristics of an exemplary passive target used in the system of FIGS. 1–3.

Each of sensor assembly 21R and 21L has its own u, v, $z_s$ co-ordinate system aligned with its associated directional infrared energy source, i.e., light emitting diodes 27L, 27R, respectively. The diodes 27L, 27R are evenly distributed circumferentially about the $z_s$ axis of each of sensor assemblies 21R and 21L. The plurality of infrared emitting diodes 27L, 27R is energized with electrical energy by a processor section 19. The processor section 19 includes a processor 26, host computer 30, display 32 and controller 18. The processor 26 energizes the diodes 27L, 27R via a signal on line 29, the plurality of infrared emitting diodes 27L, 27R operate to produce an incident directional energy beam 40I (FIG. 4) of infrared energy with a direction of propagation aimed along a directional axis which generally corresponds to the $z^s$ axis of each of the sensor assemblies 22L, 22R associated with that directional infrared energy source. The incident directional energy beam created by the directional infrared energy source is of a size, shape and intensity that corresponds to the volumetric field of view of its associated sensor 22L, 22R and sufficient to provide an incident directional energy beam throughout the measurement volume 28 (FIG. 1).

The sensor assemblies 21L, 21R are each able to produce output signals on lines 24L, 24R, respectively, which represent the intensity of energy focused thereon. During each sensor cycle, the energy focused thereon is collected (i.e. integrated) and then shifted to a processor 26. Here, the sensor assemblies 21L and 21R are mounted to a fixed reference and are separated from each other by a predetermined distance, D, (FIG. 2) here 500 mm. Here, the sensor assemblies 21L, 21R each have a field of view sufficient to observe a common measurement volume 28 of approximately 1 m³ centered along the z axis at approximately 1.9 m from the origin point which is midway between the lenses 23L and 23R.

As noted above, each of sensor assemblies 21R and 21L has its own associated lens 23L, 23R, respectively, for focusing both the reflected energy from the energy retro-reflecting targets 14a and the emitted energy from the energy emitting targets 14b, in order to create a focused energy image of the emitted or reflected energy from the targets 14b, 14a, respectively on the lens' 23L, 23R associated sensor assemblies 21R, 21L, respectively.

The processor 26 coupled to the sensors 22R and 22L determine the two-dimensional u, v positions of the focused energy image on each of the sensors 22R and 22L. Then, using the u, v position of the focused energy image of the same target 14a, 14b on each of the sensors 22R and 22L to perform mathematical computations known in the art which computations include comparing the u, v positions of the focused energy image to a data set of known spatial positions relative to the origin of a common, fixed x, y, z co-ordinate system in order to determine the spatial position the target 14a, 14b in relation to the common coordinate system. The processor 26 is coupled to the host computer 30 in order that the spatial position of the targets 14a, 14b can be displayed on display 32 or further processed by the host computer 30. As noted above, the processor 26 is coupled to the directional infrared energy sources 27L, 27R in order that the processing section 19 can activate the directional infrared energy sources 27R and 27L at appropriate times during an energy reflecting target detection mode. The processor 26 is also coupled to the controller 18 in order that the processor 26 can signal the controller 18 to activate the energy emitting targets 14b in the required manner during an energy emitting target detection mode. Thus, there are two operating modes of the system 10: an active mode (i.e., target 14b emitting mode); and a passive mode (i.e., target 14a reflecting mode). These modes may be operated in a manner to be described in detail in connection with FIGS. 5A–5D. Suffice it to say here, however, that the processor section 19 common processor for both modes and is adapted to determine the spatial positions of both the passive and active targets in response to the energy detected by the common detector (i.e., sensors 22R and 22L) during a sequence of sensor cycles. During a first portion of the sensor cycles the spatial position of the active target is determined and during a second portion of the cycles the position of the passive target is determined. The sensor cycles in the first portion may be interspersed with the sensor cycles in the second portion, or cycles in the first and second portions may overlap to enable simultaneous determination of both the active target and the passive target during a single sensor cycle. It is noted that the position of either an active target or a passive target may be determined in a single sensor cycle. Thus, the processing of a sensor cycle for active target or targets may, for example be interspersed with the processing of a sensor cycle for the passive target or targets. Further, a plurality of active target sensor cycles may occur followed by the processing of one or more passive target sensor cycles. That is, the active and passive cycles may be interspersed. Further, the sensor cycle may be the same to enable simultaneous detection of both the active target and the passive target during a single sensor cycle.

Thus, the controller 18 is provided for controlling the activation of the energy emitting targets 14b. More particularly, the controller 18 is coupled to one or more of the energy emitting targets 14b and is, upon receiving the appropriate signal or signals from the processor 26, able to activate one or more of the energy emitting targets 14b either individually, individually in a sequence specified by the processor 26, all at the same time, or in subsets specified by the processor 26 in a manner described in our co-pending patent application Ser. No. 08/603,791 entitled "System for Determining the Spatial Position and Angular Orientation of an Object", filed Feb. 20, 1996 and assigned to the same assignee as the present invention, the entire contents thereof being incorporated herein by reference.

The system 10 operates in one of a plurality of operating mode patterns as selected by the user. These patterns will be described in detail in connection with FIGS, 5A–5D. When the processor 26 operates in the energy reflecting target mode, the processor 26 activates each of the directional infrared energy sources 27L, 27R. In response to the delivery of such electrical energy, the infrared emitting diodes 27L, 27R emit energy, here infrared energy, which energy combines in an incident directional energy beam with a direction of propagation aimed along a directional axis which generally corresponds to the $z_s$ axis of the sensor assemblies 22L, 22R. The energy retro-reflecting targets 14a located in the measurement volume 15 operate to retro-reflect the incident directional energy beam. Referring again to FIG. 2, an incident directional energy beam 40I from a directional infrared energy source 27L, or 27R is reflected by a retro-reflecting target 14a such that the majority of the retro-reflected energy 40R is reflected in a manner such that it is parallel to the incident directional energy beam 40I but with the opposite direction of propagation (as opposed to simple reflection whereby, as is well known in the art, energy is reflected such that the angle between the incident energy ray and the normal to the point on the surface where said incident energy ray is reflected is equal to the angle between the reflected energy ray and the said normal to the point of reflection). Retro-reflecting as used in the invention is well known in the art. The incident directional energy beam 40I emitted by the directional infrared energy source 27L, for example, and acting upon an energy retro-reflecting target 14a will result in a reflected directional energy beam 40R having a direction of propagation only toward lens 23L, the sensor 22L and none of the reflected directional energy beam 40R propagating toward lens 23R and sensor 22R. Likewise, the incident directional energy beam 40I emitted by the directional infrared energy source 27R and acting upon an energy retro-reflecting target 14a will result in a reflected directional energy beam 40R having a direction of propagation only toward lens 23R and sensor 22R and none of the reflected directional energy beam 40R propagating toward lens 23L and sensor 22L. The reflected directional energy beam 40R is therefore propagating in the direction from whence it originated. Thus, in the case of energy initially created by the directional infrared energy source 27R, the reflected directional energy beam 40R will be collected by lens 23R and focused by lens 23R onto sensor 22R. In the passive target operating mode, the directional infrared energy sources 27L, 27R are activated by the processor 26. When a retro-reflective target 14a is situated in space such that it is within the directional beam of the directional infrared energy source (thereby illuminated by the said directional energy source) and the field of view of the CCD sensors 22L, 22R, the directional infrared energy is retro-reflected by the retro-reflective target 14a back through lenses 23L, 23R, which focus the energy image onto the CCD sensors 22L, 22R, respectively. Thus, infrared energy retro-reflected by a passive target 14a located in the field of view of the CCD sensor 22L, 22R is collected through lenses 23L, 23R, respectively, which focuses the energy image onto the CCD sensor 22L, 22R, respectively.

During the active target mode, the infrared energy emitting targets 14b are activated by the emitting target controller 18, causing the emitting targets 14b to emit infrared energy. Infrared energy emitted by an emitting target 14b located in the field of view of the CCD sensor 22L, 22R is collected through lenses 23L, 23R, respectively, which focuses the energy image onto the CCD sensor 22L, 22R, respectively.

During either the active target mode of the passive target mode, the energy image is shifted out of the two dimensional CCD sensors 22L, 22R during each cycle of the sensors 22L, 22R into the processor 26. The processor 26 is programmed to determine the position of the energy focuses image. Thus, the processor 26 uses the same processing for both the active target mode and the passive target mode to determine the spatial position of each object 12a, 12b.

Figure 5A:
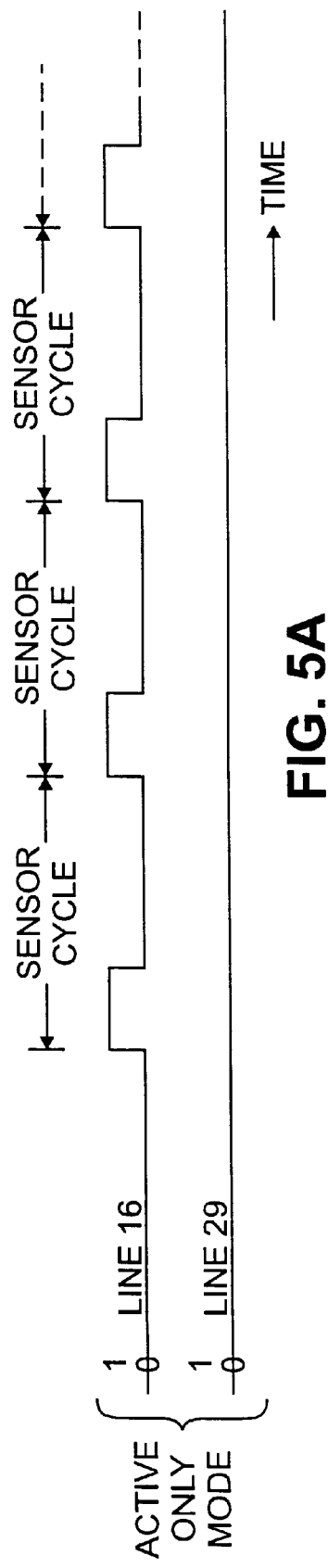
FIGS. 5A–5D are timing diagram showing the various operating patterns of the system of FIGS. 1–3, FIG. 5A showing an active only mode, FIG. 5B showing a passive only mode.
Figure 5B:
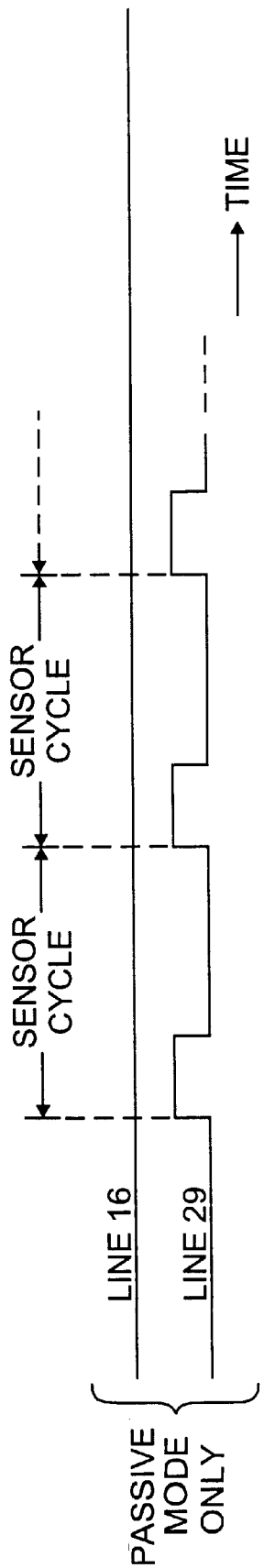
Figure 5C:
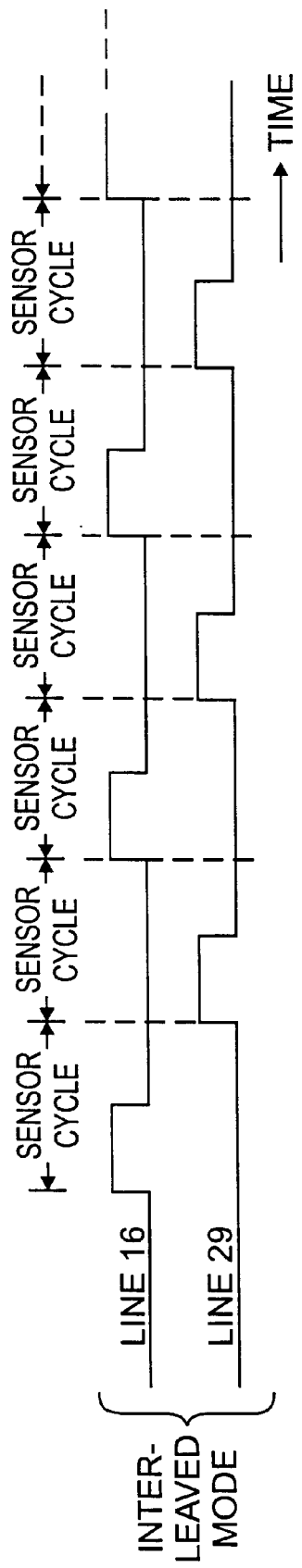
Figure 5D:
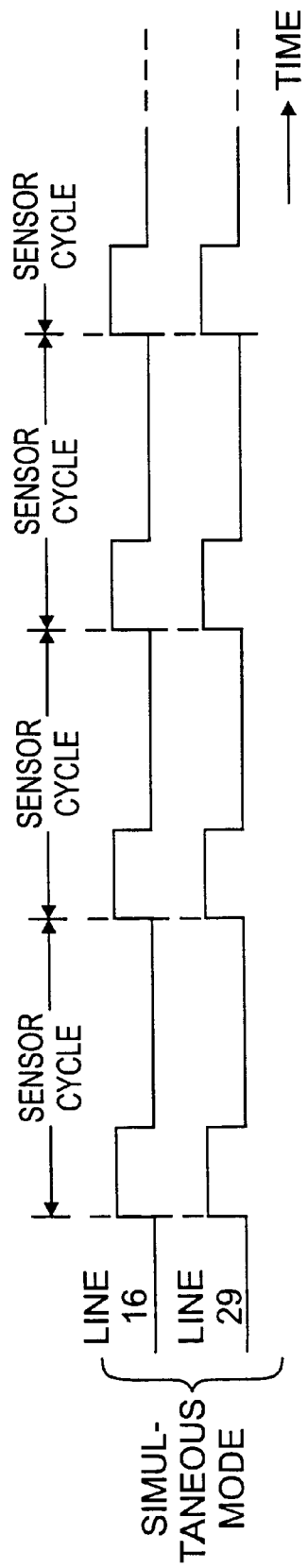

Referring to FIGS. 5A–5D various operating patterns are shown. One pattern, (i.e., an active only pattern) is shown in FIG. 5A. Here, only the targets 14b are activated via a pulse on line 16 during each of a sequence of sensor cycles. Another pattern (i.e., a passive only pattern) is shown in FIG. 5B. Here, only sources 27L, 27R are activated via a pulse on line 29 during each of a sequence of sensor cycles. Another pattern (i.e., an interspersed pattern) is shown in FIG. 5C. Here, the activation of sources 27L, 27R and the activation of targets 14b with pulses on line 29 are interspersed with pulses on line 16. Thus, here, the common processor determines the spatial positions of both the passive and active targets in response to the energy detected by the common detector during a sequence of interspersed active-passive sensor cycles. Still another pattern (i.e., a simultaneous pattern) is shown in FIG. 5D. Here, the activation of sources 27L, 27R and the activation of targets 14b with pulses on line 29 are simultaneous with the activation of targets 14b with pulses on line 16 during each of a sequence of sensor cycles. Thus, here, the common processor determines the spatial positions of both the passive and active targets in response to the energy detected by the common detector during each of a sequence of simultaneous active-passive sensor cycles.

Thus, from FIGS. 5C and 5D it is noted that during a first portion of the sensor cycles the spatial position of an active target is determined and during a second portion of the cycles the position of the passive target is determined. The sensor cycles in the first portion may be interspersed with the sensor cycles in the second portion, as in FIG. 5C, or cycles in the first and second portions may overlap to enable simultaneous determination of both the active target and the passive target during each of a sequence of single sensor cycles, as in FIG. 5D.

It is also noted from the foregoing that the use of the common detector for both the active and passive targets enables the common processor to use the same processing steps in determining the spatial orientation of both the active and passive target affixed objects.

Figure 6:
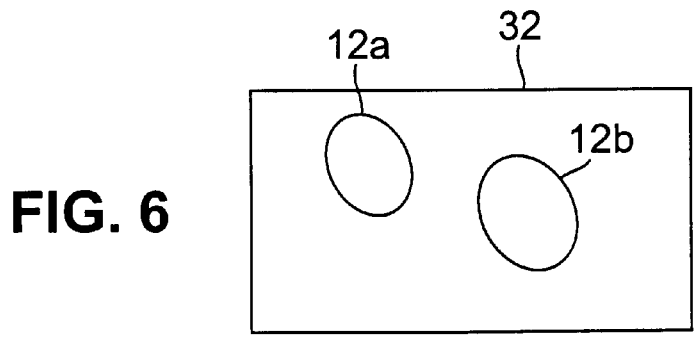
FIG. 6 is a sketch of a display used in the system of FIG. 1, such display showing a pair of objects, the spatial orientation and position of one of the objects being obtained with such object having affixed thereto active targets and the spatial orientation and position of the other one of the objects being obtained with such object having affixed thereto passive targets.

The position of each of the targets 14a and targets 14b is communicated to the host computer 30 by the processor 26. The computer 30 can be programmed to enable concurrent display of both object 12a and object 12b as shown in FIG. 6. Alternatively, the information from the computer may be stored for later display and/or further processing.

Thus, the system 10 includes: a single or a plurality of activatable emitting point targets 14b, preferably infrared emitting target points, affixable to object 12b; and/or a single or a plurality of retro-reflective point targets, preferably highly reflective retro-reflective targets, affixable to object 12a; a sensor section 20, preferably a pair of infrared sensing two dimensional array, CCD sensors, for providing signals representative of positional information of energy collected by the sensor's from either or both of emitting point targets 14b or retro-reflective point targets 14a; a processing section 19 (which includes a processor 26, preferably a microprocessor, a controller 18, and a host computer 30) responsive to the signals produced by the sensor section 20. The processing section 19 is programmed to determine the position of the active point targets 14b and/or the passive point targets 14a and for determining the spatial position of the point targets 14a, 14b and, optionally, the spatial position and orientation of objects 12a and/or 12b. The system 10 includes an energy source, preferably a plurality of directional infrared emitters 27L, 27R, fixed in relation to the sensors 22L, 22R by preferably surrounding each of the pairs of sensors 22L, 22R as assemblies 21L, 21R, respectively, where the directional beam of the emitters will illuminate the field of view of the sensors 22L, 22R it surrounds with infrared energy by directing said directional beam along an axis which corresponds to the axis projecting perpendicularly through the area centroid of the two dimensional array CCD sensor 22L, 22R. The emitters 27L, 27R are controllable to be activated as directed by the aforementioned processor section 19. The controller 18 provides for the sequenced control and activation of a plurality of emitting point targets 14b activated as directed by processor section 19.

Figure 7:
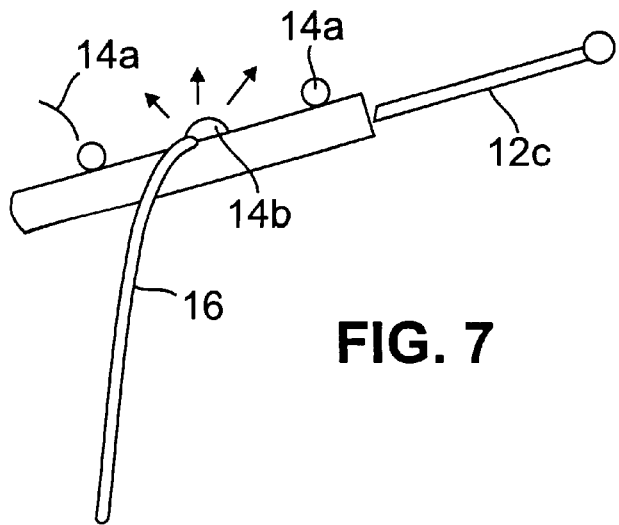
FIG. 7 shows an object having both active and passive targets affixed thereto, such targets being detectable by the system of FIG. 1.

Referring to FIG. 7 an object 12c is shown with a combination of active and passive targets adapted for detection and processing by the processor section 19. It is also noted that various combinations of passive and active targets and objects may be used, including a single passive and/or active target.

Other embodiments are within the spirit and scope of the appended claims. For example, while the determination of the location of at least three of the point targets 14a, 14b is required for 6D position and angular orientation determination, if less than a six degrees of freedom (6D) determination is desired (i.e., a position of, and a vector along, the object 12a, 12b) the determination of the location of only two of the targets 14a, 14b on each object 12a, 12b, respectively, is required. Further, while the sensor section 20 described above included a pair of spaced 2D sensors 22L, 22R, such sensor section 20 may include other sensor arrangements. For example, the sensor section 20 may include a single 2D sensor, a pair of linear sensors, or other suitable arrangement of sensors.

For example, although individual point targets are shown, here with 4 retro-reflective point targets 14a, and 4 emitting point targets 14b, the position of, and angle along, a rigid object could be determined with 2 or more retro-reflective targets 14a, or 2 or more active radiating targets 14b, or any combination of 1 or more of each retro-reflective targets 14a and active radiating targets 14b. Further, although the determination of the position and orientation of rigid objects 12a, 12b is shown here, if only the position of the object 12a or 12b is desired it can be determined with a single retro-reflective target 14a or a single active radiating target 14b. Still further, although here position sensor system 10, uses a pair of two dimensional image sensors 22L, 22R, a mathematical process is available which uses a single two dimensional image sensor 11, or two one dimensional image sensors, which can determine the position and orientation of an object with 3 or more targets, by using knowledge of the relative position of said targets and an initial estimate of the position of the object. Also, although here position sensor system 10, uses a pair of two dimensional image sensors 22L, 22R, a mathematical process is available which uses N two dimensional image sensors, where N is 2 or greater, or M one dimensional image sensors, where M is 3 or greater, which can determine the position of a target. Here, position sensor system 10 uses a pair of two dimensional image sensors 11, which are fixed in relative position and orientation, it is possible to have the image sensors free to be repositioned prior to use and a calibration sequence is employed prior to tracking the positions of point targets which will determine the relative position and orientation of the two dimensional image sensors.

What is claimed is:

1. A system for determining the spatial position of a target, comprising:

an active target adapted to emit energy in response to an active signal;

a passive target adapted to reflect energy impinging upon such passive target;

an active energy source positioned to impinge energy upon the passive target;

a common energy detector for detecting both the energy emitted by the active target and the energy reflected by the passive target; and a common processor for determining the spatial positions of both the passive and active targets in response to the energy detected by the common detector, during a first sensor cycle the spatial position of the active target being determined and during a second sensor cycle the position of the passive target being determined.

2. The system recited in claim 1 wherein the processor is adapted to intersperse a plurality of the first sensor cycles with a plurality of the second sensor cycles.

3. The system recited in claim 1 wherein the processor is adapted to have the first and second sensor cycles occur simultaneously.

4. The system recited in claim 1 wherein the processor is adapted to selectively either intersperse a plurality of the first sensor cycles cycle with the plurality of second sensor cycles or to occur simultaneously.

5. A method for determining the spatial position of a target, comprising:

affixing a passive target to an object;

affixing an active target to an object;

detecting with a common energy detector both the energy emitted by the active target and the energy reflected by the passive target;

determining with a common processor the spatial positions of both the passive and active targets in response to the energy detected by the common detector, during a first sensor cycle the spatial position of the active target being determined and during a second sensor cycle the position of the passive target being determined.

6. The method recited in claim 5 wherein the processor is adapted to intersperse a plurality of the first sensor cycles.

7. The method recited in claim 5 wherein the processor is adapted to have the first and second sensor cycles occur simultaneously.

8. The method recited in claim 5 wherein the processor is adapted to selectively either have the plurality of the first sensor cycles interspersed with the plurality of second sensor cycles or have the first and second cycles occur simultaneously.

9. A method for determining the spatial position and angular orientation of objects, comprising:

affixing a plurality of passive targets to one of the objects;

affixing a plurality of active targets to another one of the objects;

detecting with a common energy detector both the energy emitted by the active targets and the energy reflected by the passive targets;

determining with a common processor the spatial positions of both the passive and active targets in response to the energy detected by the common detector, during a first sensor cycle the spatial position of the active targets being determined and during a second sensor cycle the position of the passive targets being determined.

10. A method for determining the spatial position of an object, comprising:

affixing a passive target and an active target to the object;

detecting with a common energy detector both the energy emitted by the active target and the energy reflected by the passive target;

determining with a common processor the spatial positions of both the passive and active targets in response to the energy detected by the common detector, during a first sensor cycle the spatial position of the active target being determined and during a second sensor cycle the position of the passive target being determined.

* * * * *